United States Patent

Billoni et al.

[11] Patent Number: 5,962,508
[45] Date of Patent: Oct. 5, 1999

[54] RETINOID RECEPTOR AGONISTS FOR PROMOTING HAIR GROWTH AND/OR RETARDING HAIR LOSS

[75] Inventors: Nelly Billoni, Paris; Yann Mahe, Morsang sur Orge; Bruno Bernard, Neuilly sur Seine, all of France

[73] Assignee: Societe L'Oreal S.A., Paris, France

[21] Appl. No.: 08/925,467

[22] Filed: Sep. 9, 1997

[30] Foreign Application Priority Data

Sep. 9, 1996 [FR] France ................................. 96 10968

[51] Int. Cl.⁶ ..................................................... A61K 31/38
[52] U.S. Cl. .......................... 514/432; 514/365; 514/396; 514/408; 514/422; 514/438; 514/456; 514/461; 514/569; 514/880; 514/448
[58] Field of Search ...................... 514/448, 432, 514/365, 316, 408, 422, 438, 456, 461, 569, 880

[56] References Cited

FOREIGN PATENT DOCUMENTS

| | | |
|---|---|---|
| 0253393 | 1/1988 | European Pat. Off. . |
| 0514264 | 11/1992 | European Pat. Off. . |
| 0694301 | 1/1996 | European Pat. Off. . |
| 3903992 | 8/1990 | Germany . |
| 94/17796 | 8/1994 | WIPO . |

OTHER PUBLICATIONS

CA128:248341 Billoni et al, Mar. 18, 1998.

*Primary Examiner*—Rebecca Cook
*Attorney, Agent, or Firm*—Burns, Doane, Swecker & Mathis, L.L.P.

[57] ABSTRACT

A regimen for inducing/stimulating hair growth and/or retarding hair loss on an individual in need of such treatment, comprising administering thereto, advantageously topically and for such period of time as required to elicit the desired effect, an effective amount of at least one RXR-type retinoid receptor agonist preferably having the structural formula(I):

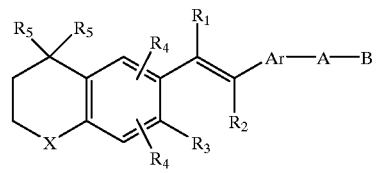

(I)

in which Ar is one of the following radicals:

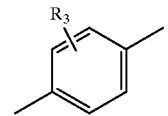

(i)

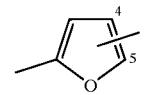

(ii)

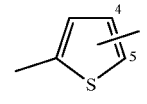

(iii)

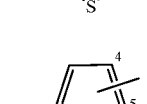

(iv)

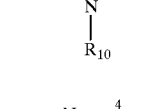

(v)

(vi)

26 Claims, No Drawings

RETINOID RECEPTOR AGONISTS FOR PROMOTING HAIR GROWTH AND/OR RETARDING HAIR LOSS

BACKGROUND OF THE INVENTION

1. Technical Field of the Invention

The present invention relates to inducing and/or stimulating hair growth and/or retarding hair loss by topically/systemically administering to an individual in need of such treatment an effective amount of at least one compound which is an agonist with respect to RXR-type retinoid receptors.

This invention also relates to novel cosmetic/therapeutic compositions comprising such retinoid receptor agonists for promoting hair growth and/or retarding hair loss.

2. Description of the Prior Art

In human subjects the growth of the hair and its renewal are principally determined by the activity of the hair follicles. This activity is cyclic and essentially entails three phases, namely, the anagenic phase, the catagenic phase and the telogenic phase.

The active anagenic phase, or growth phase, which lasts for several years and during which the hair elongates, is succeeded by a very short and transitory catagenic phase which lasts for a few weeks, followed by a rest or quiescent phase, designated the telogenic phase, which lasts for a few months.

At the end of the rest period, the hair falls out and an new cycle begins. The head of hair thus undergoes permanent renewal and, of the approximately 150,000 hairs on a human head, at any given instant, approximately 10% are at rest and will therefore be replaced within a few months.

However, various causes may lead to a considerable temporary or permanent loss of hair. Alopecia, for example, is essentially due to a disturbance of hair renewal, which leads, in a first stage, to acceleration of the frequency of the cycles at the expense of the hair quality and then at the expense of its quantity. A gradual thinning of the head of hair occurs, and the so-called "end" or "terminal" hairs at the down stage recede. Certain regions are preferentially affected, in particular the temples and the front of the head in men, and, in women, diffuse alopecia of the crown is observed.

The term "alopecia" comprehends an entire family of afflictions/conditions of the hair follicle, the final consequence of which is the permanent partial or general loss of hair. In a large number of cases, early hair loss occurs in genetically predisposed individuals and it affects men in particular. This type of hair loss is more particularly androgenetic or androgenic or, alternatively, androgeno-genetic alopecia.

Active agents for eliminating or reducing alopecia, and, in particular, for inducing or stimulating hair growth or for retarding hair loss, have long been desiderata in the cosmetics and pharmaceutical industries.

From this perspective, a great number of very diverse active compounds such as, for example, 2,4-diamino-6-piperidinopyrimidine 3-oxide or "Minoxidil," described in U.S. Pat. Nos. 4,139,619 and 4,596,812, or, alternatively, its many derivatives, such as those described, for example, in EP-0,353,123, EP-0,356,271, EP-0,408,442, EP-0,522,964, EP-0,420,707, EP-0,459,890 and EP-0,519,819, have to date been proposed.

Need continues to exist in this art, however, for other active species for modulating hair growth/loss that are more active and/or less toxic.

SUMMARY OF THE INVENTION

It has now unexpectedly and surprisingly been determined that RXR-type retinoid receptor agonists are well suited for inducing/stimulating hair growth and/or retarding hair loss.

DETAILED DESCRIPTION OF BEST MODE AND SPECIFIC/PREFERRED EMBODIMENTS OF THE INVENTION

More particularly according to the present invention, cosmetic/therapeutic compositions well suited for promoting hair growth and/or retarding hair loss are provided by formulating an effective amount of at least one RXR-type retinoid receptor agonist into appropriate cosmetically/therapeutically acceptable vehicle, diluent or carrier therefor, said at least one agonist characteristically having the following structural formula (I):

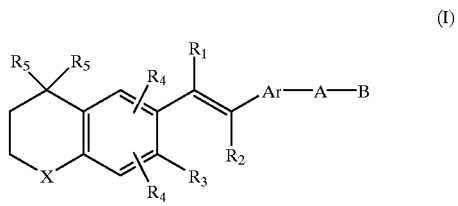

(I)

in which Ar is one of the following radicals:

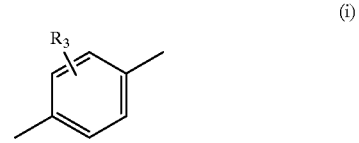

(i)

(ii)

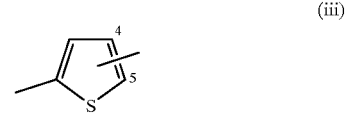

(iii)

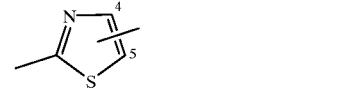

(iv)

(v)

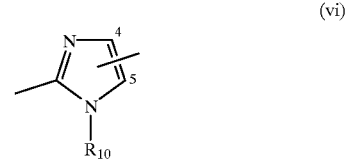

(vi)

wherein the pentagonal heterocycles are substituted in position 4 or 5; A is —$(CH_2)_n$— wherein n ranges from 0 to 5; B is a —COOH radical or a radical —$COOR_7$, —$CONR_8R_9$, —$CH_2OH$, —$CH_2OR_{10}$, —$CH_2OCOR_{10}$, —CHO, —$CH(OR_{11})_2$, —$CHOR_{12}O$, —$COR_6$, —$CR_6(OR_{11})_2$ or —$CR_6OR_{12}O$; X is an oxygen atom, the radical —C—$(R_5)_2$ or the radical $S(O)_m$ wherein m is 0, 1 or 2; $R_1$ is a halogen atom or an alkyl radical having from 1 to 6 carbon atoms; $R_2$ is a hydrogen atom or an alkyl radical having from 1 to 6 carbon atoms or a halogen atom; the radicals $R_3$, which may be identical or different, are each an alkyl radical having from 1 to 6 carbon atoms, a halogen atom or a radical —$OR_{10}$, —$SR_{10}$, —$OCOR_{10}$, —$SCOR_{10}$, —$NH_2$, —$NHR_{10}$, —$N(R_{10})_2$, —$NHCOR_{10}$ or —$NR_{10}COR_{10}$; the radicals $R_4$, which may be identical or different, are each a hydrogen atom, an alkyl radical having from 1 to 6 carbon atoms, a halogen atom, an alkoxy radical having from 1 to 6 carbon atoms or a thioalkoxy radical having from 1 to 6 carbon atoms; the radicals $R_5$, which may be identical or different, are each a hydrogen atom or an alkyl radical having from 1 to 6 carbon atoms; $R_6$ is an alkyl radical having from 1 to 6 carbon atoms, a cycloalkyl radical having from 3 to 6 carbon atoms or an alkenyl radical having from 2 to 6 carbon atoms; $R_7$ is an alkyl radical having from 1 to 10 carbon atoms, a cycloalkyl radical having from 5 to 10 carbon atoms or a phenyl or lower alkylphenyl radical; the radicals $R_8$ and $R_9$, which may be identical or different, are each a hydrogen atom, an alkyl radical having from 1 to 10 carbon atoms, a cycloalkyl radical having from 5 to 10 carbon atoms, a phenyl radical or a lower alkylphenyl radical; the radicals $R_{10}$ which may be identical or different, are each an alkyl radical having from 1 to 10 carbon atoms, a phenyl radical or a lower alkylphenyl radical; $R_{11}$ is an alkyl radical having from 1 to 6 carbon atoms; and $R_{12}$ is a divalent alkylene radical having from 2 to 5 carbon atoms; or the optical and/or geometrical isomers, acyl derivatives or pharmaceutically acceptable salts thereof, either singly or in any admixture.

The subject compounds are useful active principles for inducing and/or stimulating hair growth and/or retarding hair loss.

The compounds of formula I are described, in particular, in WO-A-94/17,796 and recognized for their agonist property with respect to RXR-type retinoid receptors.

In a preferred embodiment of the invention, the halogen atom may be a chlorine, bromine, fluorine or iodine atom, more preferably a chlorine, bromine or iodine atom.

In another preferred embodiment of the invention, $R_1$ is an alkyl radical having from 1 to 6 carbon atoms, and even more preferably $R_1$ is a methyl radical.

In another preferred embodiment of the invention, $R_2$ is a hydrogen atom or an alkyl radical having from 1 to 6 carbon atoms, and even more preferably $R_2$ is a hydrogen atom.

In yet another preferred embodiment of the invention, $R_3$ is an alkyl radical having from 1 to 6 carbon atoms, and even more preferably $R_3$ is a methyl radical.

In still another preferred embodiment of the invention, $R_4$ is a hydrogen atom or an alkyl radical having from 1 to 6 carbon atoms, and even more preferably $R_4$ is a hydrogen atom.

In still another preferred embodiment of the invention, $R_5$ is an alkyl radical having from 1 to 6 carbon atoms, and even more preferably $R_5$ is a methyl radical.

And, in yet another preferred embodiment of the invention, —A—B— is a radical —$(CH_2)_n$—$COOR_7$, or a radical —$(CH_2)_n$—$CONR_8R_9$, ($R_7$, $R_8$ and $R_9$ being defined as above) and, preferably, n is equal to zero and B is a radical —$COOR_7$.

The compounds according to the invention are preferably selected from among:

2-[(E)-2-(3,5,5,8,8-pentamethyl-5,6,7,8-tetrahydro-2-naphthyl)propen-1-yl]-4-thiophenecarboxylic acid;

2-[(E)-2-(3,5,5,8,8-pentamethyl-5,6,7,8-tetrahydro-2-naphthyl)propen-1-yl]-5-thiophenecarboxylic acid;

2-[(E)-2-(5,6,7,8-tetrahydro-3,5,5,8,8-pentamethylnaphthalen-2-yl)propen-1-yl]-4-furancarboxylic acid;

4-[(E)-2-(3,5,5,8,8-pentamethyl-5,6,7,8-tetrahydro-2-naphthyl)propen-1-yl]benzoic acid;

2-[(E)-2-(4,4,7-trimethyl-6-thiochromanyl)propen-1-yl]-4-thiophenecarboxylic acid;

ethyl 2-[(E)-2-(3,5,5,8,8-pentamethyl-5,6,7,8-tetrahydro-2-naphthyl)propen-1-yl]-4-thiophenecarboxylate;

2-[(E)-2-(3,5,5,8,8-pentamethyl-5,6,7,8-tetrahydro-2-naphthyl)propen-1-yl]-4-thiazolecarboxylic acid;

2-[(E)-2-(3,5,5,8,8-pentamethyl-5,6,7,8-tetrahydro-2-naphthyl)propen-1-yl]-5-imidazolecarboxylic acid.

A more preferred compound is 2-[(E)-2-(3,5,5,8,8-pentamethyl-5,6,7,8-tetrahydro-2-naphthyl)propen-1-yl]-4-thiophenecarboxylic azid.

These compounds may be used alone or as a mixture.

The "effective amount" of compound used obviously corresponds to the amount required to elicit the desired effect. One skilled in this art can readily determine this effective amount, which depends upon the nature of the compound and upon the individual thus treated.

To provide an order of magnitude, in the compositions according to the invention, the agonist compound is advantageously present in a concentration of from 0.001% to 10% by weight relative to the total weight of the composition and preferably from 0.01% to 1%.

The physiologically acceptable medium in which the active agent is formulated according to the invention is either anhydrous or aqueous. By the expression "anhydrous medium" is intended a solvent medium containing less than 1% of water. This medium comprises a solvent or mixture of solvents selected, more particularly, from among $C_2$–$C_4$ lower alcohols such as ethyl alcohol, alkylene glycols such as propylene glycol, alkylene glycol alkyl ethers or dialkylene glycol alkyl ethers in which the alkyl or alkylene radicals have from 1 to 6 carbon atoms. By the expression "aqueous medium" is intended a medium comprising water or a mixture of water and another physiologically acceptable solvent selected, in particular, from among the organic solvents indicated above. In the latter case, when they are present, these other solvents constitute approximately 5% to 95% of the weight of the composition.

The physiologically acceptable medium (vehicle, carrier or diluent) may contain other adjuvants and additives usually used in the cosmetic or pharmaceutical field, such as surfactants, thickeners, gelling agents, cosmetic agents, preservatives, and basifying or acidifying agents well known to this art, and in amounts which are sufficient to obtain the desired presentation form, in particular a relatively thickened lotion, a gel, an emulsion or a cream. The composition may optionally be in a form which is pressurized as an aerosol or vaporized from a pump-dispenser bottle.

It is also envisaged to include, in admixture with the active agent, compounds which further improve the activity in respect of regrowth of the hair and/or retarding hair loss, and which are already known for such activity.

Among the latter active species, particularly exemplary are:

(a) nicotinic acid esters including, in particular, tocopheryl nicotinate, benzyl nicotinate and $C_1$–$C_6$ alkyl nicotinates such as methyl or hexyl nicotinate;

(b) pyrimidine derivatives such as 2,4-diamino-6-piperidinopyrimidine 3-oxide or "Minoxidil," described in U.S. Pat. Nos. 4,139,619 and 4,596,812;

(c) agents which promote regrowth of the hair, such as those described in EP-0,648,488, assigned to the assignee hereof;

(d) antibacterial agents such as macrolides, pyranosides and tetracyclines, and in particular erythromycin;

(e) calcium antagonists such as Cinnarizine, Diltiazem, Nimodipine and Nifedipine;

(f) hormones such as estriol or analogs thereof, and thyroxine and its salts;

(g) steroidal anti-inflammatory agents such as corticosteroids (for example hydrocortisone);

(h) antiandrogens such as oxendolone, spironolactone, diethylstilbestrol and flutamide;

(i) steroidal or non-steroidal 5-α-reductase inhibitors such as finasteride;

(j) potassium agonists such as cromakalim and nicorandil.

Other such compounds include, for example, Diazoxide, Spiroxazone, phospholipids such as lecithin, linoleic and linolenic acids, salicylic acid and its derivatives described in FR-2,581,542, such as salicylic acid derivatives bearing an alkanoyl radical having from 2 to 12 carbon atoms in position 5 on the benzene ring, hydroxycarboxylic or ketocarboxylic acids and their esters, lactones and their corresponding salts, anthralin, carotenoids, eicosatetraynoic and eicosatriynoic acids or their esters and amides, vitamin D and derivatives thereof, and extracts of plant or bacterial origin.

The compositions comprising at least one compound of formula (I) may be in liposomal form, as described, in particular, in WO-94/22,468, filed Oct. 13, 1994 by Anti-Cancer Inc. Thus, the compound encapsulated in the liposomes may be delivered selectively to the hair follicle.

The pharmaceutical compositions according to the invention may be administered parenterally, enterally or topically. The pharmaceutical composition is preferably administered topically.

The cosmetic compositions according to the invention are topically applied to the alopecic areas of the scalp and the hair of an individual, and are optionally maintained in contact for several hours and, optionally, are then rinsed out. It is possible, for example, to apply a composition containing an effective amount of at least one compound of formula (I) in the evening, to maintain the composition in contact overnight and optionally to shampoo out in the morning. These applications may be repeated daily for one or more months according to the individual.

Thus, the present invention also features a regime or regimen for the cosmetic treatment of the hair and/or the scalp, comprising topically applying thereto a cosmetic composition which comprises an effective amount of at least one compound of formula (I) to the hair and/or the scalp, maintaining this composition in contact with the hair and/or the scalp and, optionally, rinsing same therefrom.

Such treatment presents the advantages of a cosmetic technique, insofar as it permits the beauty of the hair to be enhanced while at the same lime imparting greater vigor and an improved appearance thereto.

In order to further illustrate the present invention and the advantages thereof, the following specific examples are given, it being understood that same are intended only as illustrative and in nowise limitative.

EXAMPLE 1

Determination of the Effect of (E)-2-[(3,5,5,8,8-pentamethyl-5,6,7,8-tetrahydro-2-naphthyl)propen-1-yl]-4-thiorhenecarboxylic Acid on the Lengthening and Survival Time of Hair Follicles Maintained in Vitro:

Hair follicles viable in vitro were prepared according to the technique described in French patent application No. 95/08,465, filed Jul. 12, 1995 and assigned to the assignee hereof.

From a scalp biopsy, a relatively thin strip of scalp was isolated using a scalpel. The adipose tissue surrounding the follicles was removed using microtweezers, taking care not to damage the hair bulb. Under a microscope, the follicle was dissected with a scalpel in order to separate it from its epidermal and dermal environment.

The follicles were then cultured in the wells of Costar-type 24-well plates, at a rate of one follicle per well. Each well contained 0.5 ml of Williams E medium supplemented with penicillin and streptomycin to a final concentration of 50 IU/ml, glutamine to 2 mM, bovine insulin to 0.01 mg/ml and hydrocortisone to 0.04 µg/ml.

The follicles were then measured using a microscope fitted with a micrometric eyepiece.

The follicles were remeasured after 24 hours and those whose lengthening was less than 0.3 graduations of the micrometer, corresponding to 0.16 mm, were discarded.

The follicles retained for the experiment were then cultured in Williams E medium containing or not containing (E)-2-[(3,5,5,8,8-pentamethyl-5,6,7,8-tetrahydro-2-naphthyl)propen-1-yl]-4-thiophenecarboxylic acid.

Condition A: complete Williams E medium without the acid:
Condition B: complete Williams E medium+the acid at a concentration of $10^{-8}$M.

Results:

| Days | Average lengthening | Standard deviation | n | % survival |
|---|---|---|---|---|
| Condition A: | | | | |
| 0 | 0.00 | 0.00 | 11 | 100 |
| 3 | 0.96 | 0.14 | 11 | 100 |
| 4 | 1.22 | 0.20 | 11 | 100 |
| 5 | 1.48 | 0.24 | 11 | 100 |
| 6 | 1.64 | 0.28 | 11 | 100 |
| 7 | 1.85 | 0.32 | 11 | 100 |
| 10 | 2.72 | 0.34 | 8 | 73 |
| 11 | 2.97 | 0.43 | 8 | 73 |
| 12 | 3.20 | 0.49 | 8 | 73 |
| 13 | 3.47 | 0.58 | 8 | 73 |
| 14 | 3.76 | 0.62 | 8 | 73 |
| 19 | 4.89 | 0.99 | 8 | 73 |
| 21 | 5.55 | 0.95 | 8 | 73 |
| 26 | 5.75 | 0.88 | 8 | 73 |
| 27 | nd | — | 5 | 45 |
| 28 | nd | — | 4 | 36 |
| 31 | nd | — | 3 | 27 |
| 34 | nd | — | 3 | 27 |
| 35 | nd | — | 0 | 0 |
| Condition B: | | | | |
| 0 | 0.00 | 0.00 | 12 | 100 |
| 3 | 1.18 | 0.07 | 12 | 100 |
| 4 | 1.47 | 0.08 | 12 | 100 |
| 5 | 1.75 | 0.13 | 12 | 100 |
| 6 | 2.04 | 0.18 | 12 | 100 |
| 7 | 2.29 | 0.26 | 12 | 100 |
| 10 | 3.30 | 0.42 | 11 | 92 |
| 11 | 3.60 | 0.46 | 11 | 92 |
| 12 | 4.06 | 0.29 | 10 | 83 |
| 13 | 4.53 | 0.41 | 10 | 83 |
| 14 | 4.85 | 0.44 | 10 | 83 |
| 19 | 6.80 | 0.36 | 9 | 75 |
| 21 | 7.54 | 0.33 | 9 | 75 |
| 26 | nd | — | 8 | 67 |
| 27 | nd | — | 8 | 67 |

-continued

| Days | Average lengthening | Standard deviation | n | % survival |
|---|---|---|---|---|
| 28 | nd | — | 8 | 67 |
| 31 | nd | — | 7 | 58 |
| 34 | nd | — | 4 | 33 |
| 35 | nd | — | 0 | 0 |

These results demonstrate that (E)-2-[(3,5,5,8,8-pentamethyl-5,6,7,8-tetrahydro-2-naphthyl)propen-1-yl]-4-thiophenecarboxylic acid promoted lengthening of the hair follicle in culture and increased its survival time. The increase in survival time corresponds to an increase in the duration of the phase of the cycle in which hair was found and thus made it possible to delay its loss.

EXAMPLE 2

In this example, specific compositions according to the invention were formulated:

These compositions were formulated according to conventional techniques in the cosmetics or pharmacy arts.

| Lotion to combat hair loss: | |
|---|---|
| Compound of formula 1 | 0.20 g |
| Propylene glycol | 10.00 g |
| Isopropyl alcohol | qs 100.00 g |

1 ml of this lotion was applied to the scalp, at a frequency of once or twice a day.

| Lotion to combat hair loss: | |
|---|---|
| Compound of formula 1 | 0.01 g |
| Propylene glycol | 30.00 g |
| Ethyl alcohol | 40.05 g |
| Water | qs 100.00 g |

This lotion was applied to the scalp once or twice a day at a rate of 1 ml per application.

| Thickened lotion for combating hair loss: | |
|---|---|
| Compound of formula 1 | 0.20 g |
| Kawaine | 2.00 g |
| Hydroxypropylcellulose marketed by Hercules under the trademark Klucel G | 3.50 g |
| Ethyl alcohol | qs 100.00 g |

This thickened lotion was applied to the scalp once or twice a day at a rate of 1 ml per application.

| Lotion to combat hair loss: | |
|---|---|
| Compound of formula 1 | 0.05 g |
| Propylene glycol monomethyl ether marketed under the trademark Dowanol PM by Dow Chemical | 20.00 g |
| Hydroxypropylcellulose marketed by Hercules under the trademark Klucel G | 3.00 g |
| Ethyl alcohol | 40.00 g |
| Water | qs 100.00 g |

This thickened lotion was applied to the scalp once or twice a day at a rate of 1 ml per application.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for at least one of inducing or stimulating hair growth and retarding hair loss on an individual in need of treatment, comprising administering thereto, for a period of time sufficient to elicit a desired effect, an effective amount of at least one RXR-type retinoid receptor agonist.

2. The regimen as defined by claim 1, wherein said at least one RXR-type retinoid receptor agonist has the following structural formula (I):

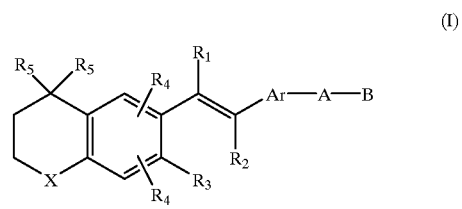

(I)

in which Ar is selected from the group consisting of the following substituents:

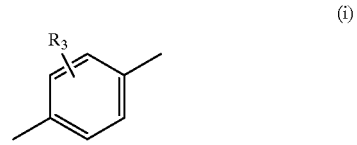

(i)

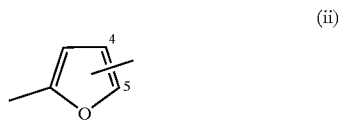

(ii)

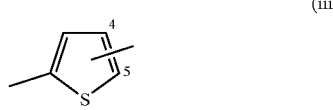

(iii)

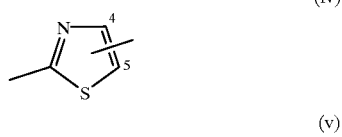

(iv)

(v)

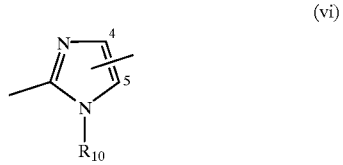

(vi)

wherein the pentagonal heterocycles (ii), (iii), (iv), (v) or (vi) are substituted in position 4 or 5; A is $-(CH_2)_n$ wherein n ranges from 0 to 5; B is $-COOH$, $-COOR_7$, $-CONR_8R_9$, $-CH_2OH$, —CH$_2$OR$_{10}$, —CH$_2$OCOR$_{10}$, —CHO, —CH(OR$_{11}$)$_2$, —CHOR$_{12}$O, —COR$_6$, —CR$_6$(OR$_{11}$)$_2$ or —CR$_6$OR$_{12}$O; X is an oxygen atom, —C(R$_5$)$_2$ or S(O)$_m$ wherein m is 0, 1 or 2; R$_1$ is a halogen atom or an alkyl substituent having from 1 to 6 carbon atoms; R$_2$ is a hydrogen atom, an alkyl substituent having from 1 to 6 carbon atoms or a halogen atom; the substituents R$_3$ are identical or different, and are each an alkyl substituent having from 1 to 6 carbon atoms, a halogen atom, —OR$_{10}$, —SR$_{10}$, —OCOR$_{10}$, —SCOR$_{10}$, —NH$_2$, —NHR$_{10}$, —N(R$_{10}$)$_2$, —NHCOR$_{10}$ or —NR$_{10}$COR$_{10}$; the substituents R$_4$ are identical or different, and are each a hydrogen atom, an alkyl substituent having from 1 to 6 carbon atoms, a halogen atom, an alkoxy substituent having from 1 to 6 carbon atoms or a thioalkoxy substituent having from 1 to 6 carbon atoms; the substituents R$_5$ are identical or different, and are each a hydrogen atom or an alkyl substituent having from 1 to 6 carbon atoms; R$_6$ is an alkyl substituent having from 1 to 6 carbon atoms, a cycloalkyl substituent having from 3 to 6 carbon atoms or an alkenyl substituent having from 2 to 6 carbon atoms; R$_7$ is an alkyl substituent having from 1 to 10 carbon atoms, a cycloalkyl substituent having from 5 to 10 carbon atoms or a phenyl or lower alkylphenyl substituent; the substituents R$_8$ and R$_9$ are identical or different, and are each a hydrogen atom, an alkyl substituent having from 1 to 10 carbon atoms, a cycloalkyl substituent having from 5 to 10 carbon atoms, a phenyl substituent or a lower alkylphenyl substituent; the substituents R$_{10}$ are identical or different, and are each an alkyl substituent having from 1 to 10 carbon atoms, a phenyl substituent or a lower alkylphenyl substituent; R$_{11}$ is an alkyl substituent having from 1 to 6 carbon atoms; and R$_{12}$ is a divalent alkylene substituent having from 2 to 5 carbon atoms; or one or more optical or geometrical isomers or acyl derivatives or pharmaceutically acceptable salts thereof.

3. The regimen as defined by claim 2, wherein in formula (I), each halogen atom is a fluorine, chlorine, bromine or iodine atom.

4. The regimen as defined by claim 2, wherein in formula (I), R$_1$ is an alkyl substituent having from 1 to 6 carbon atoms.

5. The regimen as defined by claim 2, wherein in formula (I), R$_2$ is a hydrogen atom or an alkyl substituent having from 1 to 6 carbon atoms.

6. The regimen as defined by claim 2, wherein in formula (I), each R$_3$ is an alkyl substituent having from 1 to 6 carbon atoms.

7. The regimen as defined by claim 2, wherein in formula (I), each R$_4$ is a hydrogen atom or an alkyl substituent having from 1 to 6 carbon atoms.

8. The regimen as defined by claim 2, wherein in formula (I), each R$_5$ is an alkyl substituent having from 1 to 6 carbon atoms.

9. The regimen as defined by claim 2, wherein in formula (I), —A—B— is the substituent —(CH$_2$)$_n$—COOR$_7$, or the substituent —(CH$_2$)$_n$—CONR$_8$R$_9$.

10. The regimen as defined by claim 2, wherein said at least one retinoid receptor agonist is selected from the group consisting of 2-[(E)-2-(3,5,5,8,8-pentamethyl-5,6,7,8-tetrahydro-2-naphthyl)propen-1-yl]-4-thiophenecarboxylic acid;

2-[(E)-2-(3,5,5,8,8-pentamethyl-5,6,7,8-tetrahydro-2-naphthyl)propen-1-yl]-5-thiophenecarboxylic acid;

2-[(E)-2-(5,6,7,8-tetrahydro-3,5,5,8,8-pentamethylnaphthalen-2-yl)propen-1-yl]-4-furancarboxylic acid; 4-[(E)-2-(3,5,5,8,8-pentamethyl-5,6,7,8-tetrahydro-2-naphthyl)propen-1-yl]benzoicacid; 2-[(E)-2-(4,4,7-trimethyl-6-thiochlomanyl)-propen-1-yl]-4-thiophenecarboxylic acid; ethyl 2[(E)-2-(3,5,5,8,8-pentamethyl-5,6,7,8-tetrahydro-2-naphthyl)propen-1-yl]-4-thiophenecarboxylate; 2-[(E)-2-(3,5,5,8,8-pentamethyl-5,6,7,8-tetrahydro-2-naphthyl)propen-1-yl]-4-thiazolecarboxylic acid and 2-[(E)-2-(3,5,5,8,8-pentamethyl-5,6,7,8-tetrahydro-2-naphthyl)propen-1-yl]-5-imidazolecarboxylic acid.

11. The regimen as defined by claim 2, wherein in formula (I), Ar is the substituent (i).

12. The regimen as defined by claim 2, wherein in formula (I), Ar is the substituent (ii).

13. The regimen as defined by claim 2, wherein in formula (I), Ar is the substituent (iii).

14. The regimen as defined by claim 2, wherein in formula (I), Ar is the substituent (iv).

15. The regimen as defined by claim 2, wherein in formula (I), Ar is the substituent (v).

16. The regimen as defined by claim 2, wherein in formula (I), Ar is the substituent (vi).

17. The regimen as defined by claim 2, wherein in formula (I), X is the substituent —C(R$_5$)$_2$, Ar is the substituent (iii), B is —COOH and the R substituents are alkyl or halogen.

18. The regimen as defined by claim 2, wherein said at least one retinoid receptor agonist is selected from the group consisting of 2-[(E)-2-(3,5,5,8,8-pentamethyl-5,6,7,8-tetrahydro-2-naphthyl)propen-1-yl]-4-thiophenecarboxylic acid;

2-[(E)-2-(3,5,5,8,8-pentamethyl-5,6,7,8-tetrahydro-2-naphthyl)propen-1-yl]-5-thiophenecarboxylic acid, and ethyl 2[(E)-2-(3,5,5,8,8-pentamethyl-5,6,7,8-tetrahydro-2-naphthyl)propen-1-yl]-4-thiophenecarboxylate.

19. The regimen as defined by claim 2, wherein said at least one retinoid receptor agonist is 2-[(E)-2-(5,6,7,8-tetrahydro-3,5,5,8,8-pentamethylnaphthalen-2-yl)propen-1-yl]-4-furancarboxylic acid or 4-[(E)-2-(3,5,5,8,8-pentamethyl-5,6,7,8-tetrahydro-2-naphthyl)propen-1-yl]benzoic acid.

20. The regimen as defined by claim 2, wherein said at least one retinoid receptor agonist is 2-[(E)-2-(4,4,7-trimethyl-6-thiochromanyl)propen-1-yl]-4-thiophenecarboxylic acid.

21. The regimen as defined by claim 2, wherein said al least one retinoid receptor agonist is 2-[(E)-2-(3,5,5,8,8-pentamethyl-5,6,7,8-tetrahydro-2-naphthyl)propen-1-yl]-4-thiazolecarboxylic acid or 2-[(E)-2-(3,5,5,8,8-pentamethyl-5,6,7,8-tetrahydro-2-naphthyl)propen-1-yl]-5-imidazolecarboxylic acid.

22. The regimen as defined by claim 1, comprising topically applying said a least one retinoid receptor agonist to at least one of the hair and scalp of said individual and then, optionally, rinsing said at least one retinoid receptor agonist therefrom.

23. A cosmetic or therapeutic composition of matter suited for at least one of inducing or stimulating hair growth and retarding hair loss, comprising an effective amount of at least one RXR-type retinoid receptor agonist, formulated into a cosmetically or therapeutically acceptable vehicle, diluent or carrier therefor wherein said RXR-type retinoid receptor agonist has the following structural formula (I):

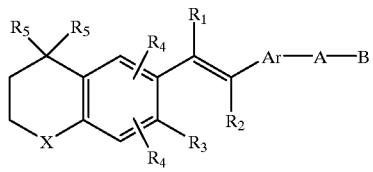
(I)

in which Ar is selected from the group consisting of the following substituents:

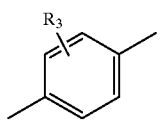
(i)

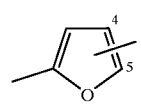
(ii)

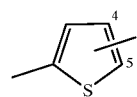
(iii)

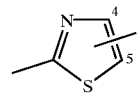
(iv)

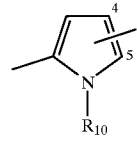
(v)

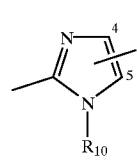
(vi)

wherein the pentagonal heterocycles (ii), (iii), (iv), (v) or (vi) are substituted in position 4 or 5; A is —(CH$_2$)$_n$ wherein n ranges from 0 to 5; B is —COOH, —COOR$_7$, —CONR$_8$R$_9$, —CH$_2$OH, —CH$_2$OR$_{10}$, —CH$_2$OCOR$_{10}$, —CHO, —CH(OR$_{11}$)$_2$, —CHOR$_{12}$O, —COR$_6$, —CR$_6$(OR$_{11}$)$_2$ or —CR$_6$OR$_{12}$O; X is an oxygen atom —C(R$_5$)$_2$ or S(O)$_m$ wherein m is 0, 1 or 2; R$_1$ is a hydrogen atom or an alkyl substituent having from 1 to 6 carbon atoms; R$_2$ is a hydrogen atom, an alkyl substituent having from 1 to 6 carbon atoms or a halogen atom; the substituents R$_3$ are identical or different, and are each an alkyl substituent having from 1 to 6 carbon atoms, a halogen atom —OR$_{10}$, —SR$_{10}$, —OCOR$_{10}$, —SCOR$_{10}$, —NH$_2$, —NHR$_{10}$, —N(R$_{10}$)$_2$, —NHCOR$_{10}$ or —NR$_{10}$COR$_{10}$; the substituents R$_4$ are identical or different, and are each a hydrogen atom, an alkyl substituent having from 1 to 6 carbon atoms, a halogen atom, an alkoxy substituent having from 1 to 6 carbon atoms or a thioalkoxy substituent having from 1 to 6 carbon atoms; the substituents R$_5$ are identical or different and are each a hydrogen atom or an alkyl substituent having from 1 to 6 carbon atoms; R$_6$ is an alkyl substituent having from 1 to 6 carbon atoms, a cycloalkyl substituent having from 3 to 6 carbon atoms or an alkenyl substituent having from 2 to 6 carbon atoms; R$_7$ is an alkyl substituent having from 1 to 10 carbon atoms, a cycloalkyl substituent having from 5 to 10 carbon atoms or a phenyl or lower alkylphenyl substituent; the substituents R$_8$ and R$_9$ are identical or different, and are each a hydrogen atom, an alkyl substituent having from 1 to 10 carbon atoms, a cycloalkyl substituent having from 5 to 10 carbon atoms, a phenyl substituent or a lower alkylphenyl substituent; the substituents R$_{10}$ are identical or different, and are each an alkyl substituent having from 1 to 10 carbon atoms, a phenyl substituent or a lower alkylphenyl substituent; R$_{11}$ is an alkyl substituent having from 1 to 6 carbon atoms; and R$_{12}$ is a divalent alkylene substituent having from 2 to 5 carbon atoms; or one or more optical or geometrical isomers or acyl derivatives or pharmaceutically acceptable salts thereof, and wherein said composition further comprises another hair growth promoter which is not a RXR-type retinoid receptor agonist.

24. The cosmetic or therapeutic composition as defined by claim 23, comprising from 0.001% to 10% by weight of said at least one retinoicd receptor agonist.

25. The cosmetic or therapeutic composition as defined by claim 23, comprising from 0.1% to 1% by weight of said at least one retinoid receptor agonist.

26. The cosmetic or therapeutic composition as defined by claim 24, comprising a lotion, gel, emulsion, cream, aerosol or spray.

* * * * *